United States Patent
Mikhailov

(10) Patent No.: US 10,610,788 B2
(45) Date of Patent: Apr. 7, 2020

(54) USER IDENTIFIED TO A CONTROLLER

(71) Applicant: Sony Interactive Entertainment Inc., Tokyo (JP)

(72) Inventor: Anton Mikhailov, Campbell, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 154 days.

(21) Appl. No.: 15/263,242

(22) Filed: Sep. 12, 2016

(65) Prior Publication Data

US 2016/0375364 A1 Dec. 29, 2016

Related U.S. Application Data

(63) Continuation of application No. 13/092,110, filed on Apr. 21, 2011, now Pat. No. 9,440,144.

(51) Int. Cl.
*A63F 13/79* (2014.01)
*A63F 13/235* (2014.01)
(Continued)

(52) U.S. Cl.
CPC ............ *A63F 13/79* (2014.09); *A61B 5/1172* (2013.01); *A63F 13/213* (2014.09); *A63F 13/22* (2014.09);
(Continued)

(58) Field of Classification Search
CPC .......... A63F 13/10; A63F 13/12; A63F 13/06; A63F 2300/6045; A63F 13/00;
(Continued)

(56) References Cited

U.S. PATENT DOCUMENTS 5,396,267 A * 3/1995 Bouton ................. A63F 13/06
345/156
6,735,695 B1 5/2004 Gopalakrishnan et al.
(Continued)

FOREIGN PATENT DOCUMENTS

CN 1977293 A 6/2007
CN 101810003 A 8/2010
(Continued)

OTHER PUBLICATIONS

European Patent Office, The Hague, "European Search Report" for Invention Patent Application No. 12163851.4, completed Oct. 3, 2012.
(Continued)

*Primary Examiner* — Patrick F Marinelli
(74) *Attorney, Agent, or Firm* — Penilla IP, APC

(57) ABSTRACT

Methods, systems, and computer programs for obtaining profile data of a user from a wearable device are provided. One example method includes connecting a peripheral device with a base computing device via a data connection. The peripheral device usable for interfacing with a computer game when executed by the base computing device. The method also includes detecting, by the peripheral device, a wearable device of a user that is using the peripheral device. The wearable device having an electronic circuit and a memory for storing information usable to identify a profile of the user. The method further includes reading or obtaining, by the peripheral device, the information from the memory of the wearable device, then sending the information to the base computing device. The information is used by the base computing device to identify the profile of the user. The profile of the user being used to obtain calibration data for the user, to avoid requiring the user to perform (Continued)

calibration each time the user interacts with the computer game.

4 Claims, 8 Drawing Sheets

(51) Int. Cl.
| | |
|---|---|
| A63F 13/22 | (2014.01) |
| A63F 13/73 | (2014.01) |
| A63F 13/213 | (2014.01) |
| A63F 13/35 | (2014.01) |
| A61B 5/1172 | (2016.01) |
| G06F 3/01 | (2006.01) |

(52) U.S. Cl.
CPC ............ *A63F 13/235* (2014.09); *A63F 13/35* (2014.09); *A63F 13/73* (2014.09); *G06F 3/017* (2013.01); *A63F 2300/1018* (2013.01); *A63F 2300/1031* (2013.01); *A63F 2300/208* (2013.01); *A63F 2300/5546* (2013.01); *G06F 3/011* (2013.01)

(58) Field of Classification Search
CPC ........ A63F 2300/406; A63F 2300/1087; A63F 13/73; A63F 2300/1031; A63F 13/40; A63F 13/79; A63F 2300/5546; A63F 2300/101; A63F 13/22–13/245; A63F 2300/403; G06F 3/038; G06F 3/0383
USPC .................... 463/1–47, 49–57; 345/156–157
See application file for complete search history.

(56) References Cited

U.S. PATENT DOCUMENTS

| | | | | |
|---|---|---|---|---|
| 6,811,491 | B1* | 11/2004 | Levenberg | A63F 13/02 273/148 B |
| 6,963,937 | B1* | 11/2005 | Kamper | G06F 3/038 345/156 |
| 6,995,745 | B2* | 2/2006 | Boon | G06F 3/016 345/156 |
| 7,330,176 | B2* | 2/2008 | Liang | G06F 3/016 345/156 |
| 8,172,675 | B2* | 5/2012 | Migos | A63F 13/06 463/29 |
| 8,192,285 | B2* | 6/2012 | Cheng | A63F 13/02 273/148 B |
| 8,754,746 | B2* | 6/2014 | Lukas | G06F 3/0383 340/5.82 |
| 2003/0048250 | A1* | 3/2003 | Boon | G06F 3/016 345/156 |
| 2003/0118216 | A1* | 6/2003 | Goldberg | G03D 15/001 382/115 |
| 2004/0161132 | A1 | 8/2004 | Cohen et al. | |
| 2005/0097595 | A1* | 5/2005 | Lipsanen | G06F 21/10 725/25 |
| 2006/0031099 | A1* | 2/2006 | Vitello | A61M 5/14212 705/2 |
| 2007/0024580 | A1* | 2/2007 | Sands | G06F 3/011 345/156 |
| 2007/0186923 | A1* | 8/2007 | Poutiatine | A61J 7/0038 128/200.14 |
| 2007/0298726 | A1 | 12/2007 | Fuqua | 455/73 |
| 2008/0015017 | A1* | 1/2008 | Ashida | A63F 13/02 463/37 |
| 2008/0300055 | A1 | 12/2008 | Lutnick et al. | |
| 2009/0012925 | A1* | 1/2009 | Brown | G06Q 30/02 706/46 |
| 2009/0027337 | A1* | 1/2009 | Hildreth | G06F 3/011 345/158 |
| 2009/0153475 | A1* | 6/2009 | Kerr | H04N 5/4403 345/157 |
| 2009/0217211 | A1 | 8/2009 | Hildreth et al. | |
| 2009/0298590 | A1* | 12/2009 | Marks | A63F 13/02 463/37 |
| 2009/0312096 | A1 | 12/2009 | Kane et al. | |
| 2010/0009755 | A1 | 1/2010 | Burckart et al. | |
| 2010/0130286 | A1 | 5/2010 | Ackley et al. | |
| 2010/0130289 | A1 | 5/2010 | Uehara et al. | |
| 2010/0134424 | A1* | 6/2010 | Brisebois | G06F 3/03547 345/173 |
| 2010/0153521 | A1* | 6/2010 | Lor | G06F 15/16 709/219 |
| 2010/0161522 | A1* | 6/2010 | Tirpak | G06F 3/016 706/11 |
| 2010/0203973 | A1 | 8/2010 | Muth | |
| 2010/0229194 | A1* | 9/2010 | Blanchard | G06F 3/038 725/39 |
| 2010/0248822 | A1* | 9/2010 | Migos | A63F 13/06 463/29 |
| 2010/0277489 | A1 | 11/2010 | Geisner et al. | |
| 2010/0285879 | A1 | 11/2010 | Huang et al. | |
| 2010/0306716 | A1 | 12/2010 | Perez | |
| 2011/0021271 | A1 | 1/2011 | Ikeda et al. | |
| 2011/0118026 | A1* | 5/2011 | Lukas | G06F 3/0383 463/37 |
| 2011/0199186 | A1* | 8/2011 | Han | G06K 19/07741 340/10.1 |
| 2011/0234488 | A1* | 9/2011 | Ge | G06F 3/014 345/156 |
| 2012/0159330 | A1* | 6/2012 | Jeong | G06F 3/017 715/716 |
| 2012/0200491 | A1 | 8/2012 | Miller, IV | |
| 2012/0268360 | A1* | 10/2012 | Mikhailov | A63F 13/06 345/156 |
| 2013/0214932 | A1 | 8/2013 | Hino et al. | |
| 2016/0375364 | A1* | 12/2016 | Mikhailov | A63F 13/06 463/29 |

FOREIGN PATENT DOCUMENTS

| | | |
|---|---|---|
| CN | 101930282 A | 12/2010 |
| CN | 101967286 A | 1/2011 |
| CN | 102008822 A | 4/2011 |
| CN | 102750434 A | 10/2012 |
| EP | 1315118 A1 | 5/2003 |
| EP | 1329838 A2 | 7/2003 |
| EP | 2529807 A1 | 12/2012 |
| JP | 2002292123 A | 10/2002 |
| JP | 2002325970 A | 12/2002 |
| JP | 2006350473 A | 12/2006 |
| JP | 2009020656 A | 1/2009 |
| JP | 2009510645 A | 3/2009 |
| JP | 2009165826 A | 7/2009 |
| JP | 2011024774 A | 2/2011 |
| JP | 2012223566 A | 11/2012 |
| KR | 1020060084165 A | 7/2006 |
| KR | 100711105 A | 4/2007 |
| TW | 200714332 A | 4/2007 |
| WO | WO03073286 A1 | 9/2003 |
| WO | WO2006003599 A1 | 1/2006 |
| WO | WO2009018161 A1 | 2/2009 |
| WO | WO2009117311 A2 | 9/2009 |
| WO | WO2009152064 A2 | 12/2009 |
| WO | WO2010129150 A2 | 11/2010 |
| WO | WO2010141376 A1 | 12/2010 |

OTHER PUBLICATIONS

International Search—Form PCT/ISA210 Citation of document, documents to be considered relevant.
JP Office Action PW120006 with English translation.
TIPO Office Action and IPO Search Report 101111107 with English Translation Aug. 15, 2014.
Third Office Action (OA3) in Chinese and English 201210119117.2 dated Dec. 4, 2015.
The Second Office Action (OA2) and Search Report in Chinese 201210119117.2 and English.

(56) References Cited

OTHER PUBLICATIONS

The First Office Action (OA1) and Search Report in Chinese 201210119117.2 dated Jan. 18, 2015 and English.
KIPO Notice of Preliminary Rejection with English translation dated May 14, 2014.
EP Application No. 12 163 851.4-1209, Ref. P100301EP JAT, Communication pursuant to Article 94(3) EPC, Jan. 1, 2018.

* cited by examiner

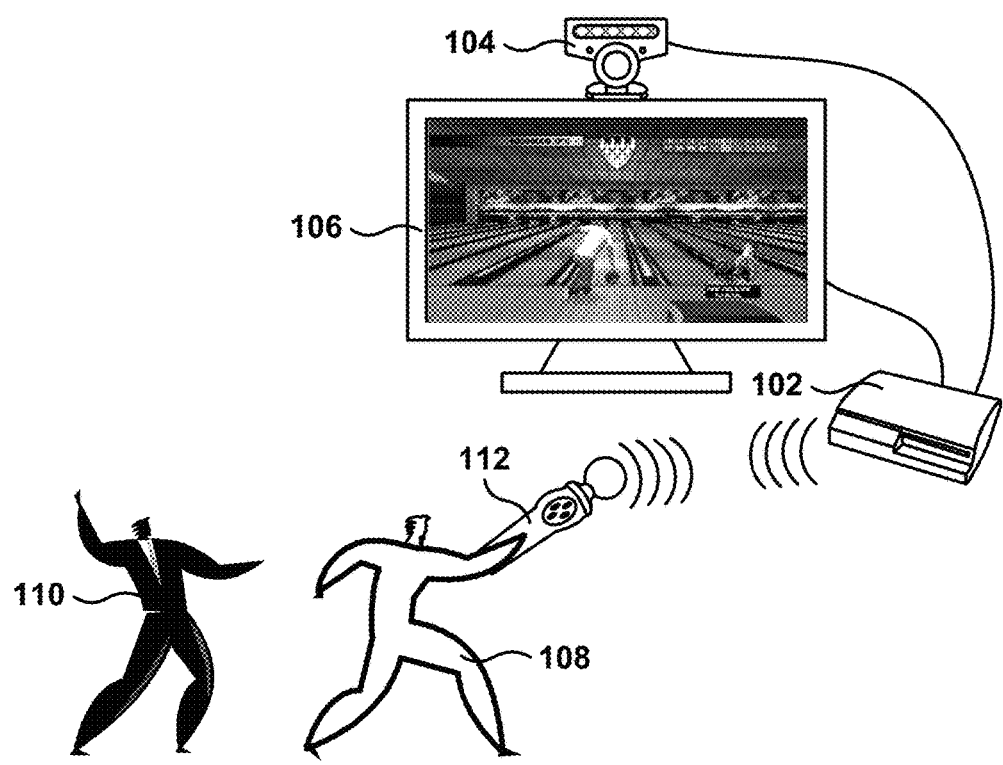
Fig. 1
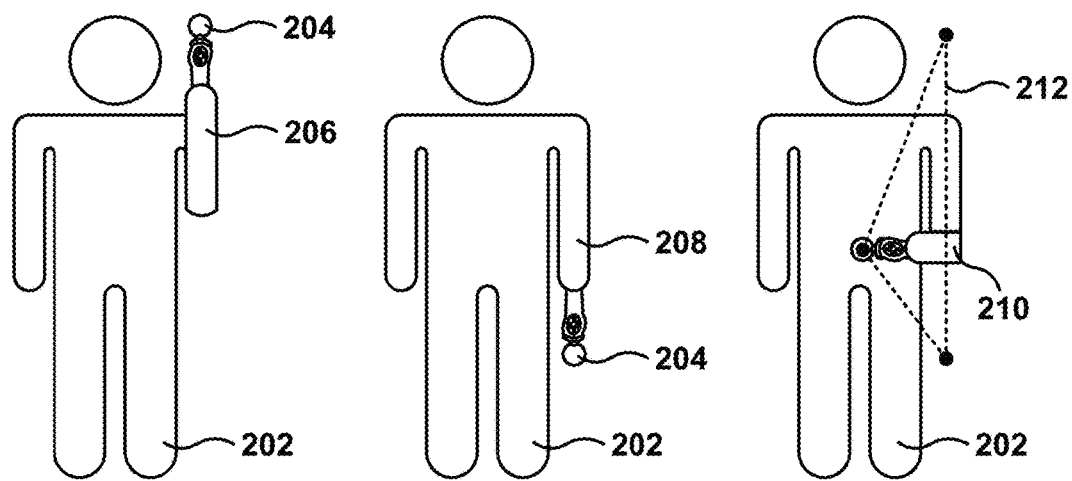
Fig. 2A    Fig. 2B    Fig. 2C

USER IDENTIFIED TO A CONTROLLER

CROSS REFERENCE TO RELATED APPLICATION

This application is a continuation application under 35 U.S.C. § 120 of U.S. patent application Ser. No. 13/092,110, filed Apr. 21, 2011 (issued as U.S. Pat. No. 9,440,144 on Sep. 13, 2016), entitled "User Identified to a Controller," which is herein incorporated by reference.

DESCRIPTION OF THE RELATED ART

A growing trend in the computer gaming industry is the development of games that increase the interaction between user and gaming system. One way of accomplishing a richer interactive experience is by utilizing wireless game controllers, whose movement is tracked by the gaming system. The movement of the controller is used as input for the game. Generally speaking, gesture input refers to the detection of a user gesture by an electronic device, e.g., computing system, video game console, smart appliance, etc., utilizing a camera tracking the user's space.

Gaming systems that track wireless controllers often use calibration operations for estimating the playing area where the player operates, as well as some of the player's physical characteristics. Calibration is important because, to offer a rewarding interactive experience, the gaming system must account for the dimensions of the player and the playing area. For example, the range of motion for a child swinging a virtual baseball bat is much smaller than the range of motion for an adult swinging the virtual bat. The gaming system must accommodate both players, so both can hit a home run.

In some games, such as golf, baseball, or bowling, two or more users take turns playing the game and sharing a controller. In order to calibrate the system properly, the calibration must be performed each time the controller changes hands. This is cumbersome and interferes with the rapid start of play when a user begins a turn.

It is in this context that embodiments arise.

SUMMARY

Embodiments of the present invention provide methods, systems, and computer programs for configuring a computer program based on user. It should be appreciated that the present invention can be implemented in numerous ways, such as a process, an apparatus, a system, a device or a method on a computer readable medium. Several inventive embodiments of the present invention are described below.

In one embodiment, a method is provided that includes connecting a peripheral device with a base computing device via a data connection. The peripheral device usable for interfacing with a computer game when executed by the base computing device. The method also includes detecting, by the peripheral device, a wearable device of a user that is using the peripheral device. The wearable device having an electronic circuit and a memory for storing information usable to identify a profile of the user. The method further includes reading or obtaining, by the peripheral device, the information from the memory of the wearable device, then sending the information to the base computing device. The information is used by the base computing device to identify the profile of the user. The profile of the user being used to obtain calibration data for the user, to avoid requiring the user to perform calibration each time the user interacts with the computer game.

In one embodiment, a method includes an operation for detecting, by a controller, an object carried by a user, where the object includes a parameter value—e.g., a radio-frequency identification (RFID) tag—that uniquely identifies the object from a plurality of objects. The parameter value is transmitted to a computing device executing the computer program, and the computer program determines if the computer program has user information associated with the transmitted parameter value. The computer program is configured utilizing the user information, when the computer program has the user information for the parameter value.

In another embodiment, a method for configuring a computer program based on user includes operations for reading, by a controller, a fingerprint of a user, and for transmitting the fingerprint to a computing device executing the computer program. Further, if the computer program has user information associated with the fingerprint, the computer program is configured utilizing the user information.

In yet another embodiment, a method for configuring a computer program based on user is presented. The method includes an operation for entering a signature detection mode by the computer program. A signature entered by the user is detected, the user entering the signature by moving a controller. After exiting the signature detection mode, the computer program determines if the computer program has user information associated with the signature entered by the user. If the computer program has the user information for the signature entered by the user, a new calibration is set for the controller in the computer program based on the user information.

In one embodiment, a controller, for configuring a computer program based on user, includes a radio-frequency identification (RFID) reader, a memory, and a processor. The RFID reader is operable to detect an RFID tag in an object carried by a user, with the RFID tag uniquely identifying the object from a plurality of objects. Further, the processor is operable to transmit the RFID tag to a computing device executing the computer program, where the computer program is operable to search for user information associated with the RFID tag. In addition, the computer program is configured utilizing the user information when the search obtains the user information associated with the RFID tag.

Other aspects will become apparent from the following detailed description, taken in conjunction with the accompanying drawings.

BRIEF DESCRIPTION OF THE DRAWINGS

The invention may best be understood by reference to the following description taken in conjunction with the accompanying drawings.

FIG. 1 shows two players taking turns playing a game, according to one embodiment.

FIGS. 2A-2C illustrate an embodiment for calibrating a user to a controller.

DETAILED DESCRIPTION

Figure 3A:
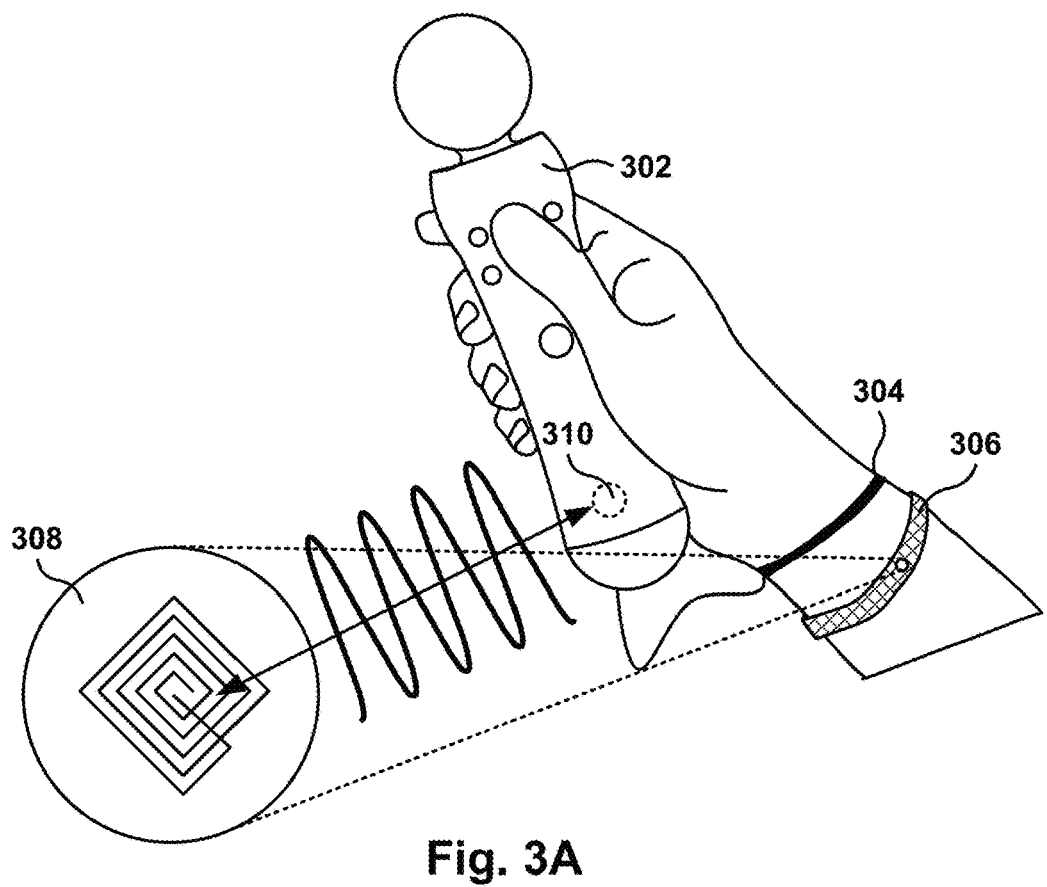
FIG. 3A shows a bracelet, having a Radio-Frequency IDentification (RFID), which identifies the user to a controller, according to one embodiment.

The following embodiments describe methods, apparatus, and computer programs for configuring a computer program based on user. It will be apparent, that the present embodiments may be practiced without some or all of these specific details. In other instances, well known process operations have not been described in detail in order not to unnecessarily obscure the present embodiments.

FIG. 1 shows two players taking turns playing a game, according to one embodiment. Player 108 is playing a bowling game with game console 102 and utilizing wireless controller 112. Camera 104 and game console 102 implement a controller tracking system to follow the movement of controller 112 in a three-dimensional space. As the user 108 moves controller 112, camera 104 is taking images of the play area. Game console 102 analyzes the captured images to track the movement of controller 112. The controller tracking system may include other elements, besides the camera, to track the controller motions, such as gyroscopes, magnetometers, accelerometers, ultrasound emitters and receivers, light emitters, etc. It is noted that the embodiment illustrated in FIG. 1 is exemplary. Other embodiments may utilize different tracking systems, and the embodiment illustrated should therefore not be interpreted to be exclusive or limiting, but rather exemplary or illustrative.

In the embodiment of FIG. 1, when user 108 is ready to play, the user moves the controller in a circular motion next to his body to simulate the throwing of a virtual bowling ball. The action in the virtual bowling game is shown on display 106. Oftentimes, two or more players—such as players 108 and 110 in the embodiment of FIG. 1—play the game by taking turns. At each turn, the player throws the virtual bowling ball and then passes controller 112 to the other player.

However, the controller tracking system needs to be calibrated for each player. Since the game executing in console 102 does not know which player is holding the controller, the calibration has to be performed at each turn so the controller tracking system obtains data for the tracking, e.g., the location and size of the player. In one embodiment, the game performs a calibration operation for each player and then assumes that the correct player is the one holding the controller at the corresponding turn. However, this may become a problem if a player decides to let other player take a turn. For example, if a child wants her father to throw the bowling ball for her, the tracking system may produce incorrect responses since the range of motion of a child can be much smaller than the range of motion of an adult.

Although the embodiment of FIG. 1 is described for a bowling game, turn taking may occur in other games, such as baseball, golf, puzzles, etc., or in single-player games because the players decide to take turns.

Embodiments of the invention provide methods and systems to identify the user that is holding a controller, allowing the game console to avoid or minimize the number of calibrations required to play the game when multiple users participate in the game. Once a user passes the controller to another user and the game recognizes the change, the parameters of the game, including calibration, are changed to match the current user holding the controller.

FIGS. 2A-2C illustrate an embodiment for calibrating a user to a controller. In general, the goal of calibration is to identify the playing area where the user will be interacting with the game, and the physical characteristics of the user, such as size, height, body center, etc. Some calibrations may capture additional information, such as age and weight, used to configure parameters of the game, e.g., fitness, expected reaction times, user progress over time, language, etc.

It should be noted that calibration, as used herein, may refer to a set of parameters associated with a user for tracking motions of the user (i.e., a calibration of the user includes values for the user-related parameters used in tracking), or calibration may refer to the process by which the calibration parameters may be obtained. Typically, the initial calibrating process performs certain calibrating operations (e.g., see FIGS. 2A-2C) that initializes the calibration parameters for the user. As discussed below, in some embodiments, the calibration parameters may be updated without requiring a new calibrating process by leveraging other types of information that identify the user or the playing area.

FIGS. 2A-2C shows the three stages of a three-stage calibration. In the first stage shown in FIG. 2A, user 202 holds controller 204 upwards next to the user's face, with the arm held in a vertical position 206 and the elbow bent. In the second stage shown in FIG. 2B, user 202 holds controller 204 downwards next to the user's body, with the arm held in vertical position 208 and a straight elbow. In the third stage shown in FIG. 2C, user 202 holds controller 204 at his waist, approximately at the center of the body, with the arm in horizontal position 210 and the elbow bent towards the body.

Using the image capture device, the game console determines the three positions of the controller at the three stages. The three positions for the ball in the controller form triangle 212, which is used by the computer program to determine the user's size, which includes, in one embodiment, the height and center of the user.

It is noted that the calibration illustrated in FIGS. 2A-2C is exemplary, and other calibrations may utilize different user motions and different number of stages. The embodiment illustrated in FIGS. 2A-2C should therefore not be interpreted to be exclusive or limiting, but rather exemplary or illustrative.

In another embodiment, a simplified calibration may follow the calibration described above. For example, a player may perform the three-stage calibration at the beginning of the game, and later in the game, when another user passes the controller, the game may do a simple one-stage calibration by placing the controller as shown in FIG. 2A, or by using a two-stage calibration as shown in FIGS. 2A and 2B. The information from the simple calibration is combined with the original three-stage calibration to update the player's calibration parameters. For example, the first calibration calculates the height and center of the player, and a second calibration is used to determine the approximate location of the player.

FIG. 3A shows a bracelet, having a Radio-Frequency IDentification (RFID), which identifies the user to a controller, according to one embodiment. RFID uses radio communication to exchange data between a reader and an electronic tag attached to an object, for the purpose of identification and tracking. RFID involves interrogators (also known as readers), and tags (also known as labels). Most RFID tags contain at least two components. The first component is an integrated circuit for storing information, processing information, modulating a radio-frequency (RF) signal, demodulating the RF signal, etc. The second component is an antenna for receiving and transmitting the signal.

There are three types of RFID tags: passive RFID tags, active RFID tags, and battery assisted passive (BAP) RFID tags. Passive RFID tags have no power source and require an external electromagnetic field to initiate a signal transmission. Active RFID tags contain a battery and can transmit signals once an external source (referred to as an interrogator) has been successfully identified, and BAP RFID tags require an external source to wake up, but have a greater range. Some embodiments are described below using passive RFID tags, but other types of RFID tags may be used.

In FIG. 3A, bracelet 306 has RFID tag 302, and controller 302 has RFID reader 310. RFID reader 310 obtains the value of RFID tag 302 using RFID techniques, and transmits the tag value to the game console, which uses the tag value to identify the player holding controller 302. In another embodiment, controller 302 holds a table of RFID tags and the users associated with each tag, and the user recognition process is performed at the controller. Controller 302 and the game console exchange the user information to adjust the calibration for the current user holding the controller. Tether 304 is used to safely attach controller 302 to the wrist of the player, which prevents accidental drops or throws of controller 302.

In one embodiment, the game console performs a calibration procedure the first time each player holds the controller in a game session, such as the calibration procedure described above with reference to FIGS. 2A-2C. Afterwards, each time the controller changes hands, assuming that all players are wearing a bracelet, the RFID tag is read and the calibration values of the player associated with the tag are used to configure the game or computer program executing in the console.

In another embodiment, information from the current player and information from the player that previously held the controller are combined. For example, the game may assume that the new player will be playing in the same physical space as the previous player, and the game parameters maintained from the previous player may include, for example, angular direction and distance with reference to the camera for the player. On the other hand, some characteristics of the new player are configured in the game to adjust game parameters, which may include physical aspects of the player (e.g., height and center), name, avatar, etc. In yet another embodiment, a quick calibration is performed each time a controller changes hands, as previously described.

The calibration parameters for a given user may be obtained with a combination of methods using parameters obtained during an initial calibration of the user, parameters obtained during a short calibration, or parameters obtained when calibrating other users of the system. Therefore, it is possible to have a player begin a turn while playing a game without having to perform a new calibration, by using parameters obtained during the initial calibration, parameters associated the player playing the game previously, or by using an algorithm to estimate the value of some parameters (e.g., one player has been playing on the left side of the playing area, while a second player has been playing on the right side of the playing area, such as every time they pass the controller, the system also changes the play area where the player is expected to be).

Configuring the game for a player that just received the controller may include one or more of setting physical characteristics for tracking (e.g., height and center for the player), retrieving game status for the player (e.g., score, game progress, lives left, avatar, voice simulation, etc.), setting user parameters (e.g., age, sex, weight, photo, etc.), and any other user-related parameter that may be configurable in the game.

It is noted that not all players must have a bracelet to play the game. If a user does not have a bracelet, the game may use other forms of identification (see for example entering a signature with reference to FIG. 5, fingerprinting with reference to FIG. 6A, face recognition with reference to FIG. 7, etc.). In other embodiment, a user may be required to perform a calibration each time the player receives the controller if no method of identification is available. Thus, different methods of identification can be used by different players, and the system does not require choosing a single method for all players while playing a game.

It is noted that the embodiment illustrated in FIG. 3 is exemplary. Other embodiments may utilize different communication technologies, such as BlueTooth, WiFi, infrared, ultrasound, etc., or a combination thereof. Generally speaking, any wireless communication protocol, and any wireless signal handling technique can be used, including using more than one communication type to exchange information. The embodiment illustrated in FIG. 3 should therefore not be interpreted to be exclusive or limiting, but rather exemplary or illustrative. Additionally, the embodiment of FIG. 3 has been described using a bracelet, but the RFID tag can be present in any object that the user is wearing or carrying, such as a ring, a watch, a pair of glasses, a phone, a necklace, an earring, a glove, a hair clip, a card, a credit card, a wallet, a button, a key chain, an item of clothing, etc.

The communication protocols described herein can include any number of protocols. The protocols can be defined by a single standard or by multiple standards. In one embodiment, communication is performed using combined protocols. For instance, packets can be exchanged between the receiving device and the transmitting device using one protocol or two protocols. The exchange of packets can also occur in an interleaved manner, where one protocol communicates certain packets while another protocol communicates other packets. In still another embodiment, some protocols can be used to transmit packet identifiers, headers, footers, or security codes that identify a particular device as being appropriate for a specific computing device. The packet identifiers or security codes can be encrypted, or interleaved between communication sessions or exchanges between the device and a computing system. In still another embodiment, the packets can be provided to identify user information and session information which are stored in a database, either locally or on a server. The session information can be used to identify or validate the registration of a particular device, such as a handheld device.

Figure 3B:
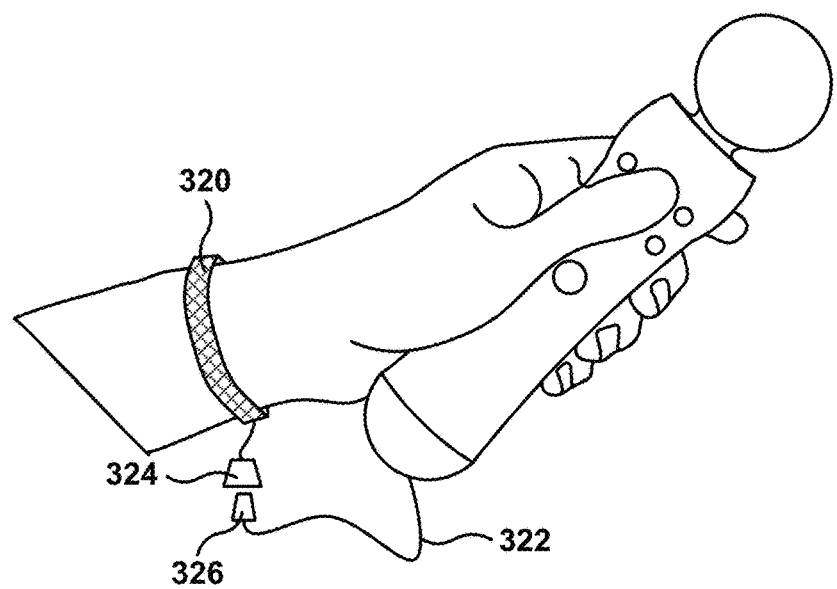
FIG. 3B shows a bracelet with a clip for attaching the bracelet to a controller, in accordance with one embodiment.

FIG. 3B shows a bracelet with a clip for attaching the bracelet to a controller, in accordance with one embodiment. Clip 324 snaps on or off clip 326 attached to the controller via cord 322. In one embodiment, the connection between clips 324 and 326 is only mechanical, allowing the bracelet to become part of the tether to safeguard accidental drop of the controller. In another embodiment, the connection to bracelet 320 is mechanical and electrical. Thus, bracelet 320 is in electrical communication with the controller and the controller can read a value stored in the bracelet. This value can be stored in a memory, an electronic circuit, etc.

As a player's turn comes up, the player snaps clip 324 to clip 326 and the identification of the player takes place, via RFID, memory read operation, or via any of the other identification methods described herein. At the end of the player's turn, the player disconnects snap 324 from snap 326.

Figure 4:
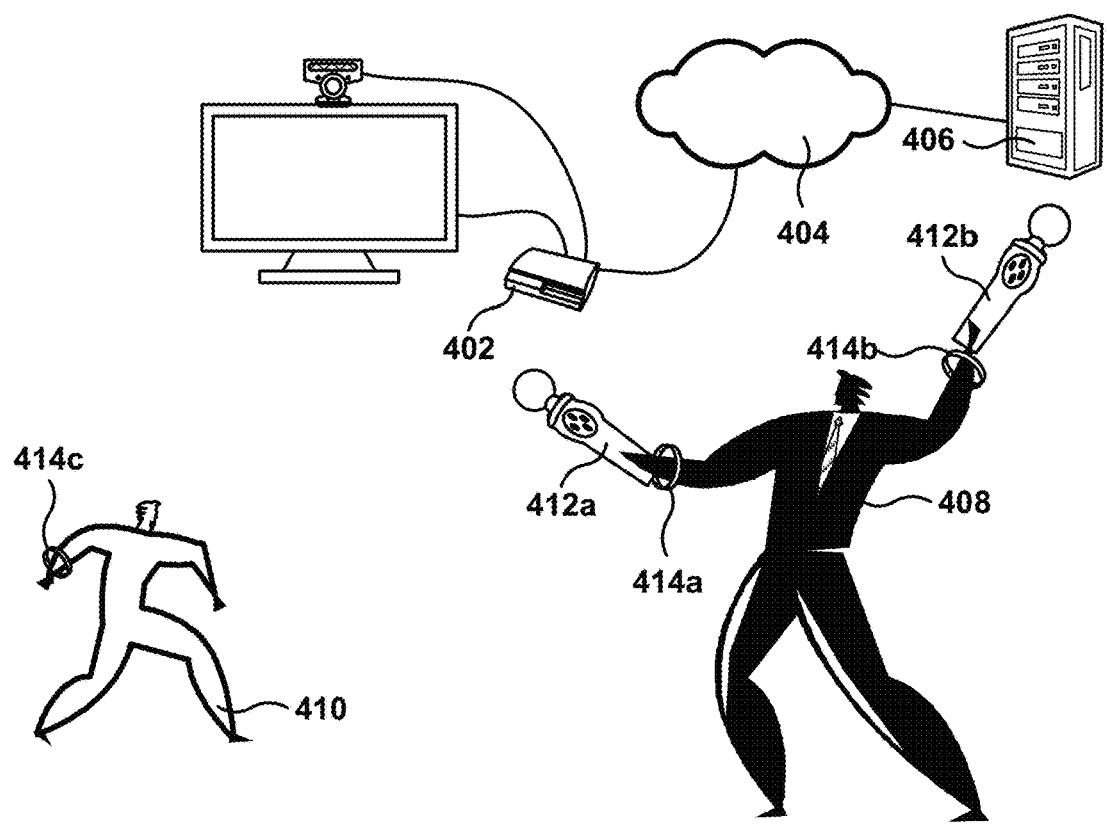
FIG. 4 shows a player holding two controllers and wearing two bracelets, according to one embodiment.

FIG. 4 shows a player holding two controllers and wearing two bracelets, according to one embodiment. Player 408 is playing a game using controllers 412a and 412b, each held in a different hand, and player 408 is wearing bracelets 414a and 414b, one in each wrist. As previously described, the system associates the user with a controller based on the bracelet near the controller.

In another embodiment, a user, holding two controllers, wears only a single bracelet. For example, player 410 is waiting for a turn to play the game, and Player 410 is wearing a single bracelet 414c. When player 410's turn comes up, the controllers are passed from player 408 to 410. The system then associates the two controllers with the single bracelet and the single user. Sometimes, both controllers may be able to read the RFID tag in the bracelet (or in some other article carried by the user), but other times only one controller may be able to read the RFID tag. In one embodiment, when only a single controller obtains the RFID tag, the system assumes that the same user is holding both controllers. In another embodiment, the system asks the user to bring both controllers together so the second controller can also read the RFID tag.

The information in the bracelet, (e.g., the RFID tag, memory contents, bar code) may also be used to retrieve user information, even the first time that the user plays a game in console 402, by retrieving information from a remote location, such as a remote server or other computing device in the network. Once console 402 retrieves the bracelet information, console 402 checks if there is local information about a user associated with the bracelet information. In another embodiment, console 402 also checks for user information in user information server 406, accessed via network 404, even if user information is found locally in console 402.

If there is no local information about the user, but information is retrieved from information server 406, console 402 uses the retrieved information to configure the game for this user. For example, console 402 may require a simplified calibration (or no calibration, as described above) from this user after obtaining the user's physical characteristics from the server. The program may also retrieve history information for this user, such as user ranking, items collected in the game, handicap, age, etc. The embodiment shown in FIG. 4 shows a user with two bracelets, but users are not limited to one or two bracelets, as users can have many bracelets or articles carrying the user information. The system tracks all the items that are associated with the single user. For example, the bracelets may be decorative and the user may select a bracelet of a certain color to match her mood or clothing, or the user may decide to wear a ring or a pendant instead, etc. In one embodiment, the system includes an option to change the user associated with the bracelet, in case the bracelet changes hands and a different user starts using the bracelet.

It is noted, that the profile information for the user can be global information, which may be used by any console on the network, or local information, which is used solely by the console running the game. Once the user finishes playing, the profile information for the user can be updated in information server 406, or can be updated locally in the console, or can be wiped out entirely.

Figure 5:
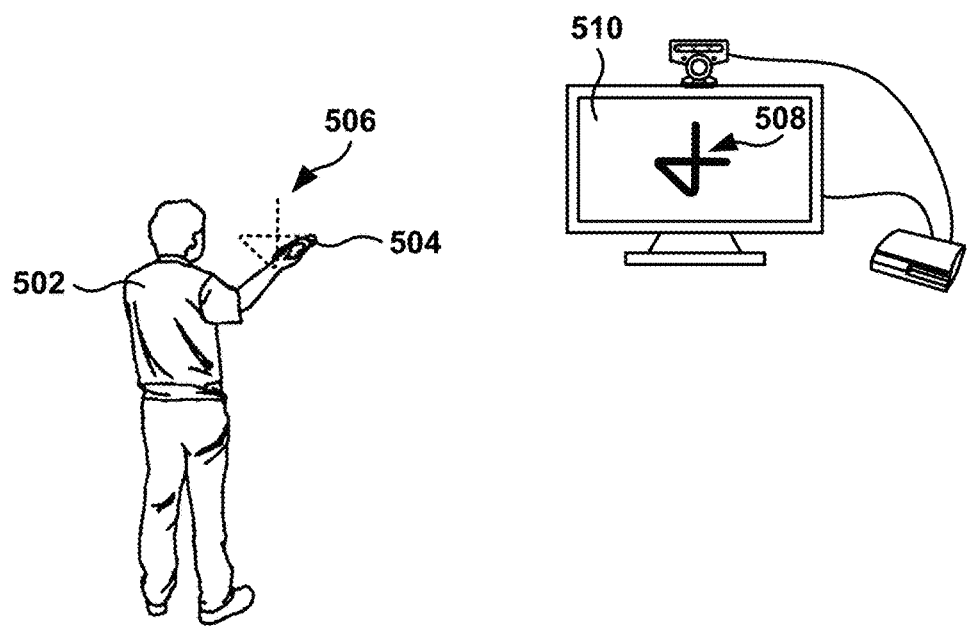
FIG. 5 illustrates the mapping of a user to a controller using signature recognition, according to one embodiment.

FIG. 5 illustrates the mapping of a user to a controller using signature recognition, according to one embodiment. When users exchange controllers, the computer program uses signature recognition to determine the identity of the new user holding the controller. In one embodiment, the user aims the controller towards display 510 and moves the controller in the air to generate signature 506. As the user moves the controller in the air, the motion is replicated 508 in display 510. In other words, the user has the impression to be writing on the display using the controller, as if the controller were a writing instrument by pointing the controller towards the display.

In one embodiment, each user defines her own signature, and an initialization process is created to enter the signature of each user in the system. During play, each user enters her signature to identify herself to the computer program. It is understood that the system allows a certain amount of deviation in the signature, because humans will not enter a perfect signature each time.

In another embodiment, the system assigns each user a distinct geometric figure (e.g., a circle, a square, a triangle, a cross, a diagonal line, a spiral, etc.), and then each user uses the assigned geometric figure when it is the user's turn to play.

Figure 6A:
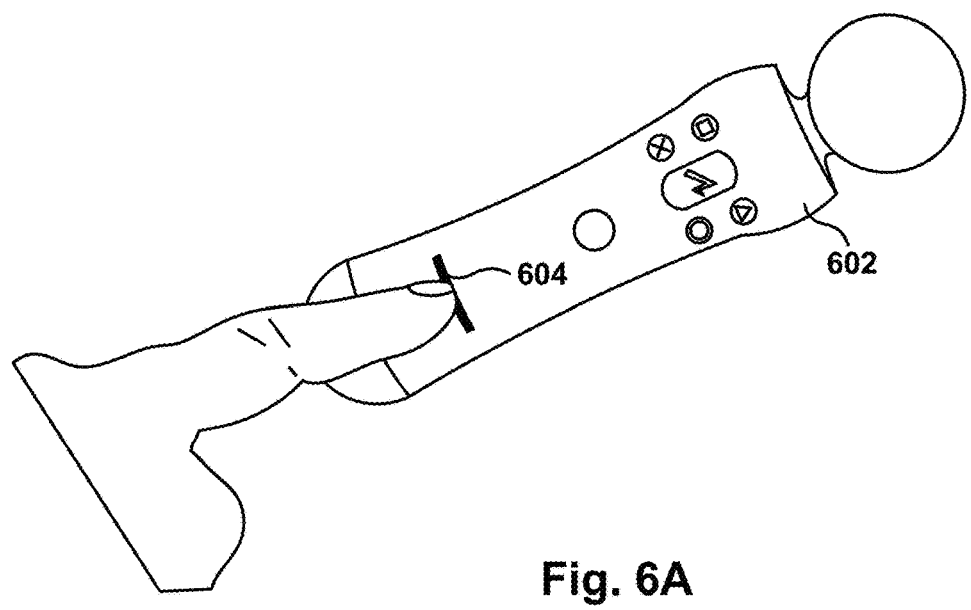
FIGS. 6A-6B show two embodiments for identifying a user by her fingerprint.
Figure 6B:
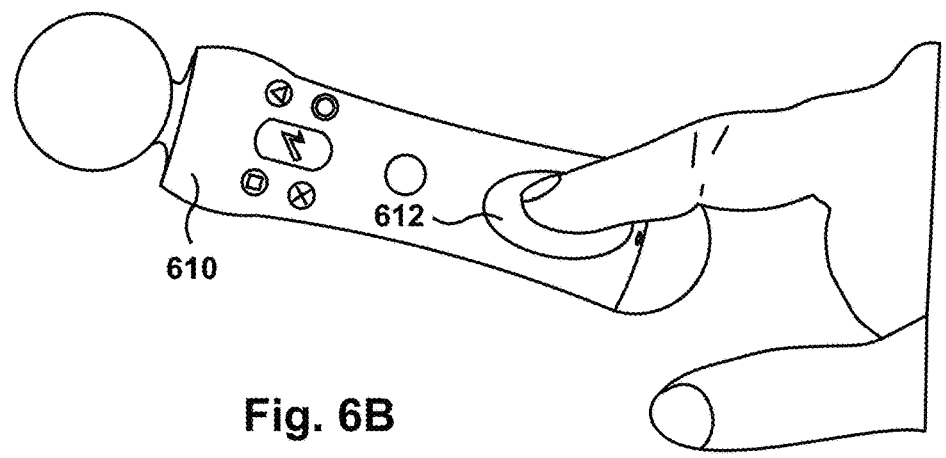

FIGS. 6A-6B show two embodiments for identifying a user by her fingerprint. FIG. 6A depicts controller 62 with slide fingerprint reader 604, and FIG. 6A shows controller 610 with optical fingerprint reader 612. It is noted that the embodiments illustrated in FIGS. 6A and 6B are exemplary. Other embodiments may utilize different fingerprint sensors and different techniques to capture fingerprints (e.g., camera, capacitance sensor, ultrasonic sensor, etc). The embodiments illustrated in FIGS. 6A and 6B should therefore not be interpreted to be exclusive or limiting, but rather exemplary or illustrative.

When a player's turn comes up, the controller captures the player's fingerprint and determines the player's identity. In one embodiment, the fingerprint information is sent from the controller to the game console, which uses a fingerprint recognition algorithm to determine if there is user information for the captured fingerprint. In another embodiment, the fingerprint system in the controller includes memory and logic to store fingerprints, and to determine if an input fingerprint corresponds to one of the fingerprints in the system. If a match is made, the controller sends the user information or identification to the game console, instead of sending the fingerprint.

In another embodiment, the fingerprint information is used to determine if the player has access privileges to a feature of the computer program. For example, the game console will play a demo version of a game if the user has not purchased the game, but the game console will play a full version of the game if the user has already purchased the game. In another embodiment, the system determines if a user is one of the users with access to certain privilege. For example, a user may be a member of a family that has purchased a game, and any of the members of the family will be given access to the game when the system detects a fingerprint from a family member.

Figure 7:
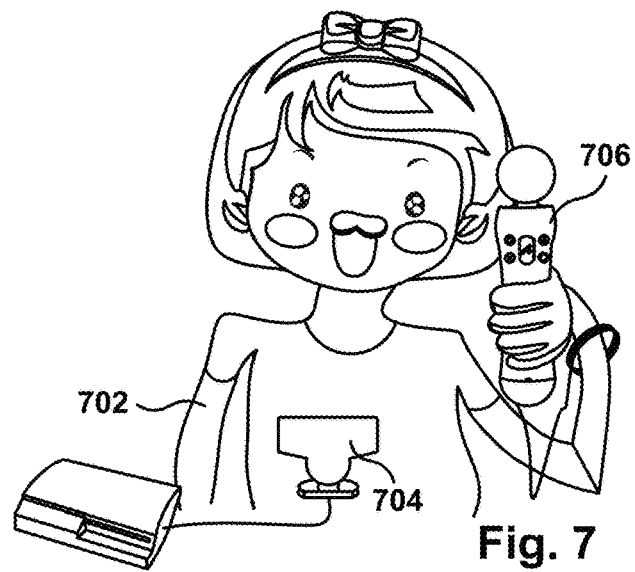
FIG. 7 illustrates user identification utilizing face recognition, according to one embodiment.

FIG. 7 illustrates user identification utilizing face recognition, according to one embodiment. When using face recognition, an image or images from camera 704 are analyzed to determine the user identity. When the user's turn to play comes up, the image from camera 704 is analyzed to find a face near the controller. The face recognition program at the game console analyzes the face to determine which of the players is holding the controller. In one embodiment, the player holds the controller 706 next to her face to perform the face recognition operation. Using the controller tracking system, the system identifies the location of the controller and analyzes the area near the controller to find facial features. Once facial features are found, the face recognition program will determine the identity of the user, if such identity exists in the system.

In another embodiment, face recognition is combined with calibration. For example, face recognition starts when the user is calibrating the controller, as seen in FIG. 2A. Since the user is holding the controller next to the face, the system captures the image of the face and stores the face image for later use in face recognition.

Figure 8:
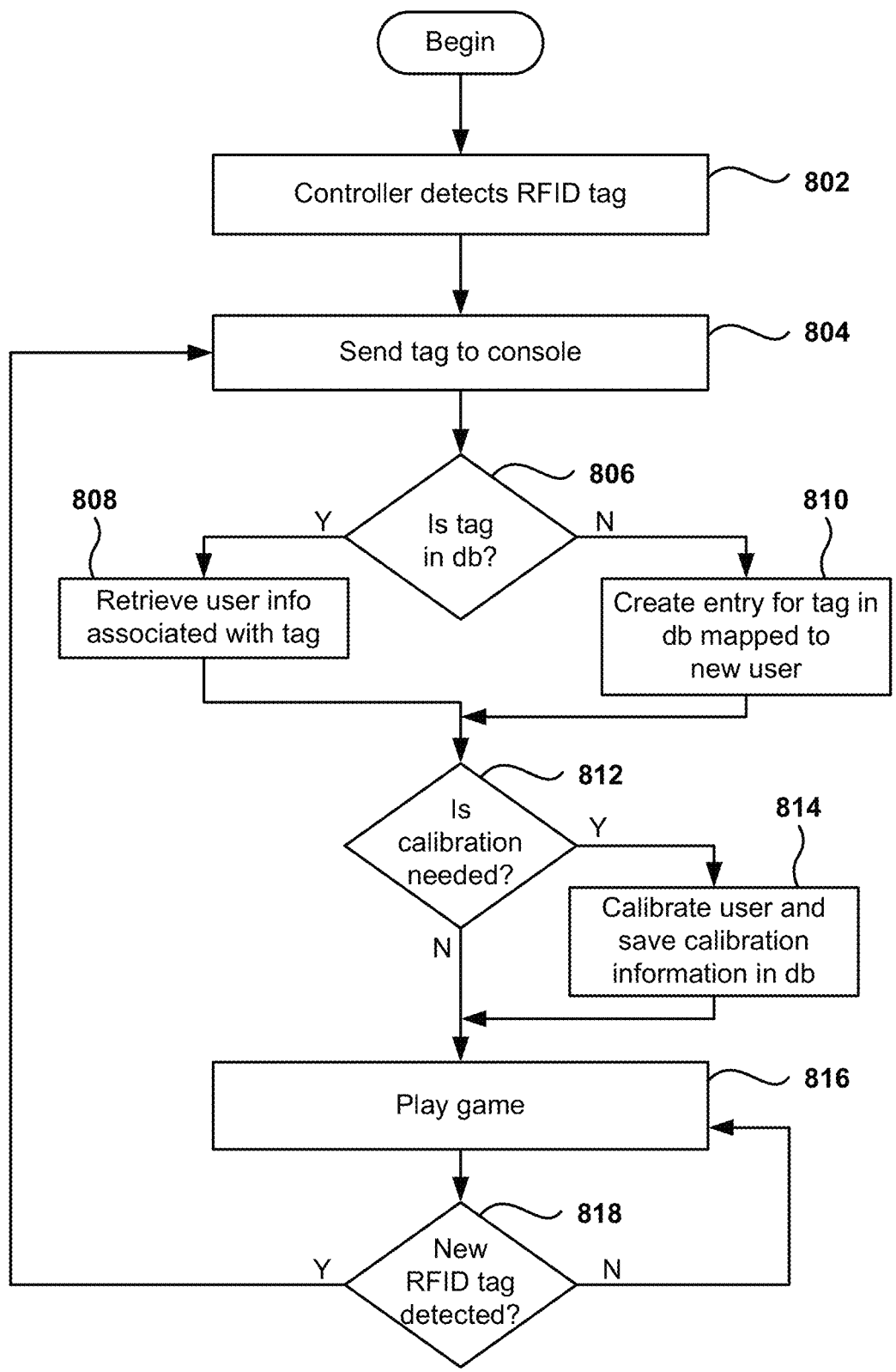
FIG. 8 shows the flowchart of an algorithm for identifying players using RFID technology, in accordance with one embodiment of the invention.

FIG. 8 shows the flowchart of an algorithm for identifying players using RFID technology, in accordance with one embodiment of the invention. In operation 802, the controller detects an RFID tag situated near the controller. After reading the tag, the controller sends the tag to the game console in operation 804. The game console checks, in operation 806, if the received tag is in the database, that holds tag and user information. If the tag is in the database, the method proceeds to operation 808, where the information of the user associated with the tag is retrieved from the database. If the tag is not in the database, the method proceeds to operation 810, where a new entry is created in the database for this tag. As the user captures user information (e.g., age, height, name), the database is updated with the captured information.

After operation 808 or 810, the method flows to operation 812 to determine if a calibration is needed. If a calibration is needed, the calibration is performed for the user, and the results of the calibration saved on the database, in operation 814. After operation 812 or 814, the method proceeds to operation 816, where the game is played.

While playing the game, the system periodically checks, in operation 818, if a new RFID tag has been detected. If the new tag has not been detected, the method returns to operation 816 to continue game play. However, if the new tag is detected, the method flows back to operation 804.

Figure 9:
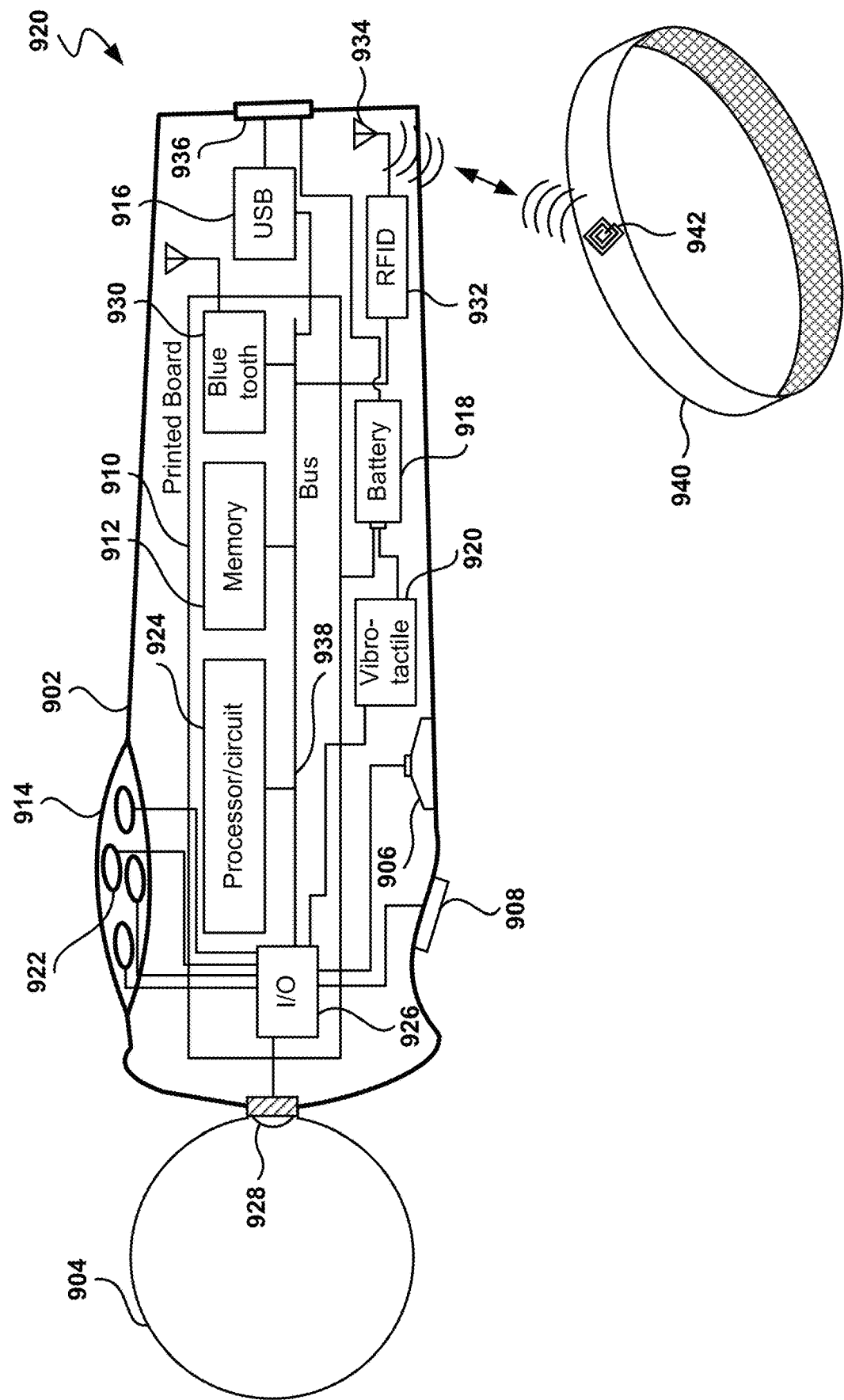
FIG. 9 is a simplified schematic diagram of a computer system for implementing embodiments of the present invention.

FIG. 9 is a simplified schematic diagram of a computer system for implementing embodiments of the present invention. FIG. 9 includes controller 920 and bracelet 940. Although controllers defined within the spirit and scope of the claims may have more or less components, these exemplary components show example electronics, hardware, firmware, and housing structure to define an operable example. These example components, however, should not limit the claimed inventions, as more or fewer components are possible. With this in mind, the controller includes body 902 (that is hand-held) and spherical section 904, also referred to herein as a ball. Body 902 is configured to provide a handle to operate controller 920 with a single hand. A user's second hand may, of course, be used to hold or select buttons on body 902. A user holding controller 920 can provide input by pressing buttons, such as top button 922 and bottom button 908, and by moving the controller within a three-dimensional space. Controller 920 is configured to operate wirelessly, which facilitates freedom of controller movement in order to interact with the base station device. Wireless communication can be achieved in multiple ways, such as via Bluetooth® wireless link, WiFi, infrared (not shown) link, or visually by capturing images of the device by a camera attached to the base computing device.

Visual communication is enhanced by the relatively large ball 904 facing the camera and that can be illuminated to improve visual recognition. Using a spherical section improves visual recognition as the ball is always perceived as a circle (or partial circle) in a captured image, independent of the orientation of the controller. Ball 904 is illuminated by light emitting device 928. In one embodiment, light emitting device 928 can emit light of a single color, and in another embodiment, light emitting device 28 can be configure to emit light from a choice of colors. In yet another embodiment, ball 904 includes several light emitting devices, each device being capable of emitting light of one color. Light emitting device 928 is configurable to emit different levels of brightness. In one embodiment, the light emitting device is an LED, which is situated at one end of the controller, such that if ball 904 is deformed by user interaction, the deformation of ball 904 will not cause damage on the LED. The base computing device can provide interactivity to the user holding the controller by changing the light emitting status of ball 904, producing audio signals, or with vibrotactile feedback, etc. One or a combination of these feedback operations are possible.

Inside body 902, printed circuit board 910 holds processor 924, Input/Output (I/O) module 926, memory 912, WiFi module (not shown), and Bluetooth module 930, interconnected by bus 938. A Universal Serial Bus (USB) module 916 also provides interactivity with the base computing device, or other devices connected to USB port 936. The USB port can also be used to charge the rechargeable battery 918. Vibrotactile feedback is provided by vibrotactile module 920.

Note that the above controller configuration and methods of operation are exemplary and many modifications thereto, including reordering some elements and/or performing some operations in parallel, would occur to a person of ordinary skill in the art with access to the present Specification, and is well within the scope of the claimed invention. For example, controller 920 can also include sensors for mechanical tracking of the controller movement.

Bracelet 940 includes RFID tag 942. It is noted that some embodiments have been presented for a bracelet with an RFID tag, where the bracelet and the RFID are exemplary. Other embodiments may include the RFID tag in other articles worn or carried by a user, such as a ring, a watch, a pair of glasses, a phone, a necklace, an earring, a glove, a hair clip, a card, a credit card, a wallet, a button, a key chain, an item of clothing, etc. In addition, the information associated with the article associated with the user may be obtained utilizing other types of wireless communication (e.g., as Bluetooth, WiFi), or obtained from other type of media, such as a memory. The embodiments illustrated should therefore not be interpreted to be exclusive or limiting, but rather exemplary or illustrative.

Figure 10:
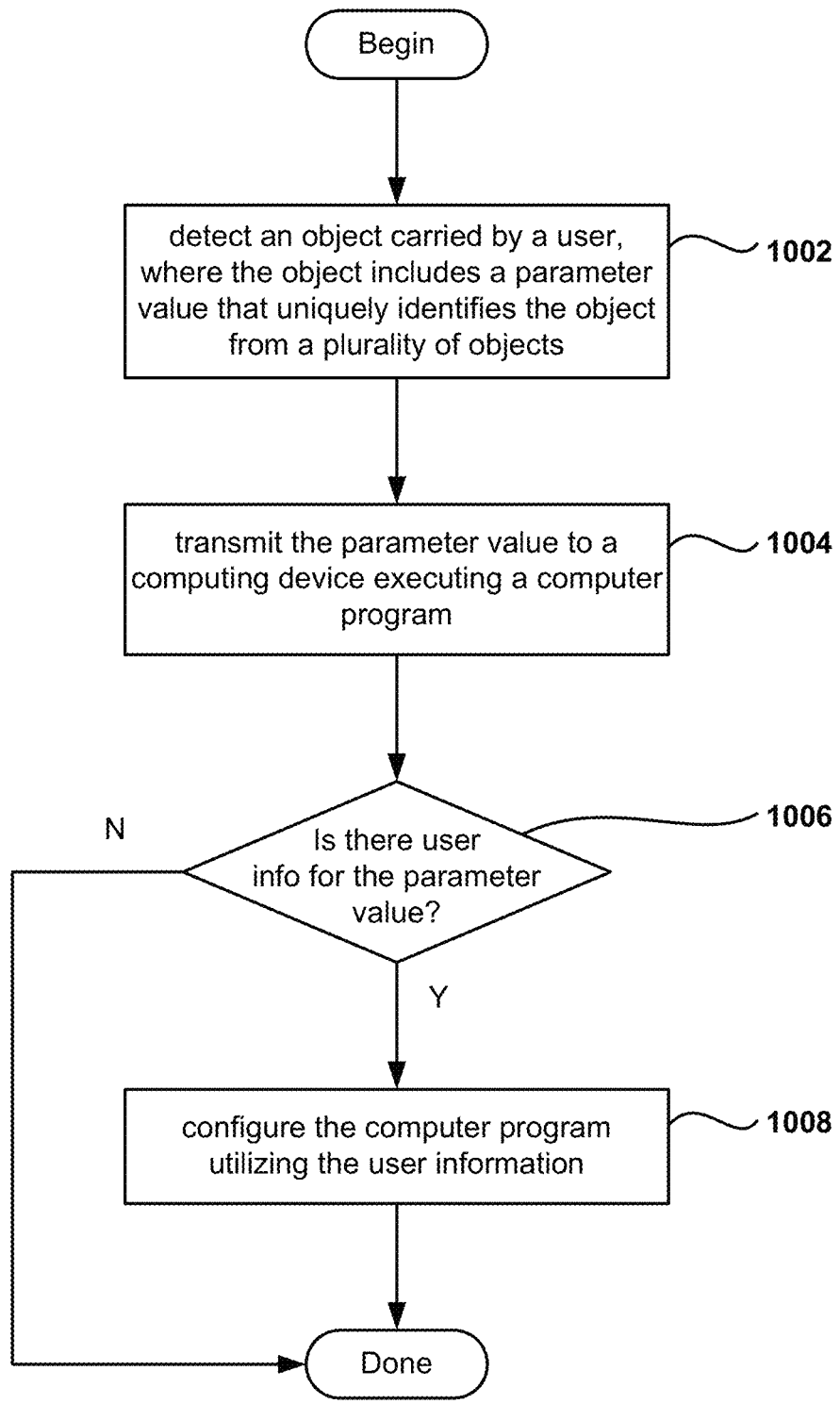
FIG. 10 shows the flowchart of an algorithm for configuring a computer program based on user, in accordance with one embodiment of the invention.

FIG. 10 shows the flowchart of an algorithm for configuring a computer program based on user, in accordance with one embodiment of the invention. In operation 1002, an object carried by a user is detected, such as the bracelet 306 of FIG. 3A. The object includes a parameter value (e.g., RFID tag, bits stored in memory, etc.) that uniquely identifies the object from a plurality of objects.

From operation 1002 the method proceeds to operation 1004, where the parameter value is transmitted to a computing device executing a computer program (e.g., gaming console 102 of FIG. 1). In operation 1006, a check is performed to determine if there is user information in the computer program associated with the parameter value. If there is user information for the parameter value, the computer program is configured utilizing the user information.

Figure 11:
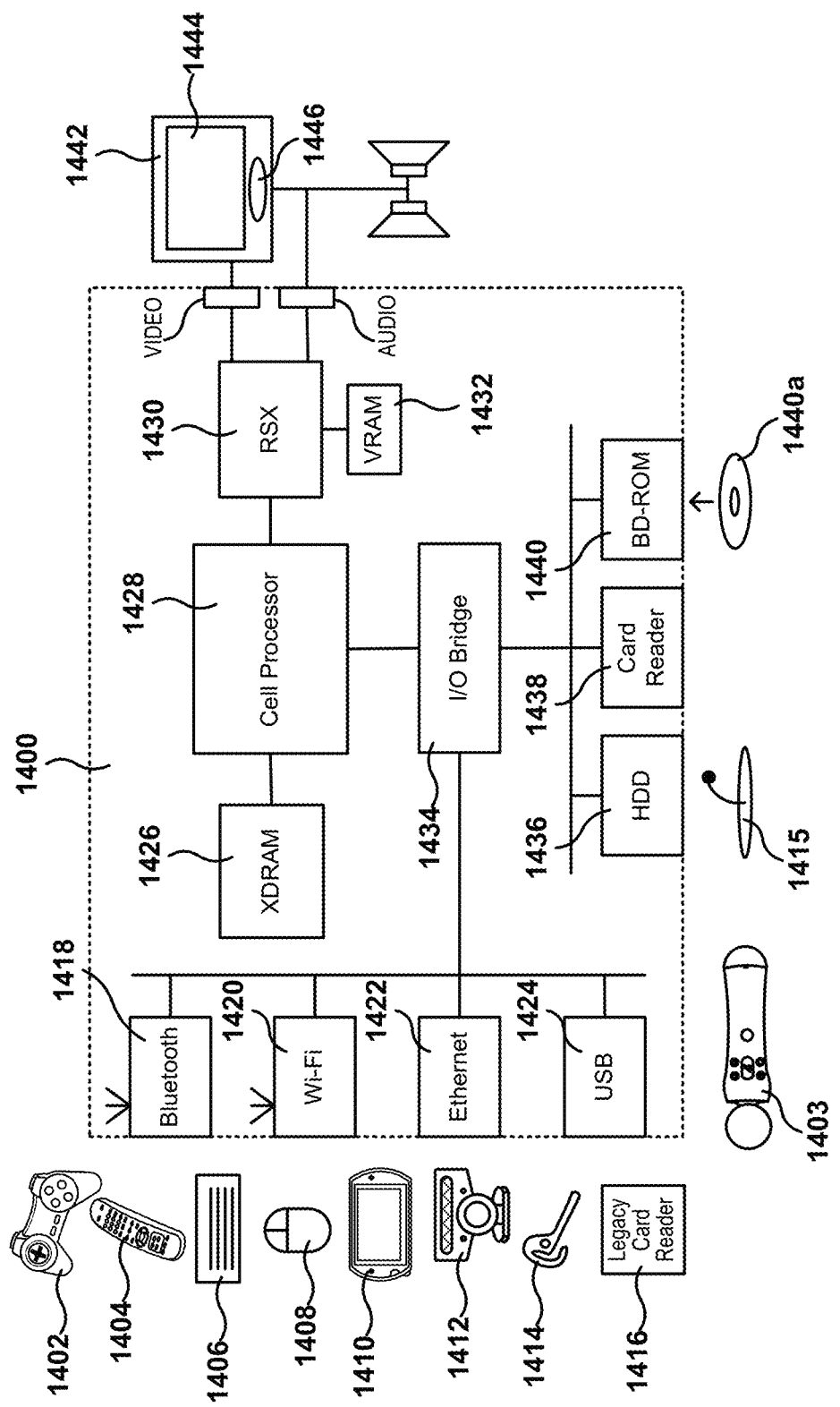
FIG. 11 illustrates hardware and user interfaces that may be used to identify users, in accordance with one embodiment of the present invention.

FIG. 11 illustrates hardware and user interfaces that may be used to identify users, in accordance with one embodiment of the present invention. FIG. 11 schematically illustrates the overall system architecture of the Sony® Playstation 3® entertainment device. A system unit 1400 is provided, with various peripheral devices connectable to the system unit 1400. The system unit 1400 comprises: a Cell processor 1428; a Rambus® dynamic random access memory (XDRAM) unit 1426; a Reality Synthesizer graphics unit 1430 with a dedicated video random access memory (VRAM) unit 1432; and an I/O bridge 1434. The system unit 1400 also comprises a Blu Ray® Disk BD-ROM® optical disk reader 1440 for reading from a disk 1440a and a removable slot-in hard disk drive (HDD) 1436, accessible through the I/O bridge 1434. Optionally the system unit 1400 also comprises a memory card reader 1438 for reading compact flash memory cards, Memory Stick® memory cards and the like, which is similarly accessible through the I/O bridge 1434.

The I/O bridge 1434 also connects to six Universal Serial Bus (USB) 2.0 ports 1424; a gigabit Ethernet port 1422; an IEEE 802.11b/g wireless network (Wi-Fi) port 1420; and a Bluetooth® wireless link port 1418 capable of supporting of up to seven Bluetooth connections.

In operation, the I/O bridge 1434 handles all wireless, USB and Ethernet data, including data from one or more game controllers 1402-1403. For example when a user is playing a game, the I/O bridge 1434 receives data from the game controller 1402-1403 via a Bluetooth link and directs it to the Cell processor 1428, which updates the current state of the game accordingly.

The wireless, USB and Ethernet ports also provide connectivity for other peripheral devices in addition to game controllers 1402-1403, such as: a remote control 1404; a keyboard 1406; a mouse 1408; a portable entertainment device 1410 such as a Sony Playstation Portable® entertainment device; a video camera such as an EyeToy® video camera 1412; a microphone headset 1414; and a microphone 1415. Such peripheral devices may therefore in principle be connected to the system unit 1400 wirelessly; for example the portable entertainment device 1410 may communicate via a Wi-Fi ad-hoc connection, whilst the microphone headset 1414 may communicate via a Bluetooth link.

The provision of these interfaces means that the Playstation 3 device is also potentially compatible with other peripheral devices such as digital video recorders (DVRs), set-top boxes, digital cameras, portable media players, Voice over Internet Protocol (IP) telephones, mobile telephones, printers and scanners. In addition, a legacy memory card reader 1416 may be connected to the system unit via a USB port 1424, enabling the reading of memory cards 1448 of the kind used by the Playstation® or Playstation 2® devices.

The game controllers 1402-1403 are operable to communicate wirelessly with the system unit 1400 via the Bluetooth link, or to be connected to a USB port, thereby also providing power by which to charge the battery of the game controllers 1402-1403. Game controllers 1402-1403 can also include memory, a processor, a memory card reader, permanent memory such as flash memory, light emitters such as an illuminated spherical section, LEDs, or infrared lights, microphone and speaker for ultrasound communications, an acoustic chamber, a digital camera, an internal clock, a recognizable shape facing the game console, and wireless communications using protocols such as Bluetooth®, WiFi™, etc. The recognizable shape can be in a shape substantially of a sphere, a cube, parallelogram, a rectangular parallelepiped, a cone, a pyramid, an imperfect sphere, a soccer ball, a football or rugby ball, an imperfect sphere, a section of a sphere, a truncated pyramid, a truncated cone, a baseball bat, a truncated cube, a polyhedron, a star, etc., or a combination of two of more of these shapes.

Game controller 1402 is a controller designed to be used with two hands, and game controller 1403 is a single-hand controller with a ball attachment. In addition to one or more analog joysticks and conventional control buttons, the game controller is susceptible to three-dimensional location determination. Consequently gestures and movements by the user of the game controller may be translated as inputs to a game in addition to or instead of conventional button or joystick commands Optionally, other wirelessly enabled peripheral devices such as the Playstation™ Portable device may be used as a controller. In the case of the Playstation™ Portable device, additional game or control information (for example, control instructions or number of lives) may be provided on the screen of the device. Other alternative or supplementary control devices may also be used, such as a dance mat (not shown), a light gun (not shown), a steering wheel and pedals (not shown) or bespoke controllers, such as a single or several large buttons for a rapid-response quiz game (also not shown).

The remote control 1404 is also operable to communicate wirelessly with the system unit 1400 via a Bluetooth link. The remote control 1404 comprises controls suitable for the operation of the Blu Ray™ Disk BD-ROM reader 1440 and for the navigation of disk content.

The Blu Ray™ Disk BD-ROM reader 1440 is operable to read CD-ROMs compatible with the Playstation and PlayStation 2 devices, in addition to conventional pre-recorded and recordable CDs, and so-called Super Audio CDs. The reader 1440 is also operable to read DVD-ROMs compatible with the Playstation 2 and PlayStation 3 devices, in addition to conventional pre-recorded and recordable DVDs. The reader 1440 is further operable to read BD-ROMs compatible with the Playstation 3 device, as well as conventional pre-recorded and recordable Blu-Ray Disks.

The system unit 1400 is operable to supply audio and video, either generated or decoded by the Playstation 3 device via the Reality Synthesizer graphics unit 1430, through audio and video connectors to a display and sound output device 1442 such as a monitor or television set having a display 1444 and one or more loudspeakers 1446. The audio connectors 1450 may include conventional analogue and digital outputs whilst the video connectors 1452 may variously include component video, S-video, composite video and one or more High Definition Multimedia Interface (HDMI) outputs. Consequently, video output may be in formats such as PAL or NTSC, or in 720p, 1080i or 1080p high definition.

Audio processing (generation, decoding and so on) is performed by the Cell processor 1428. The Playstation 3 device's operating system supports Dolby® 5.1 surround sound, Dolby® Theatre Surround (DTS), and the decoding of 7.1 surround sound from Blu-Ray® disks.

In the present embodiment, the video camera 1412 comprises a single charge coupled device (CCD), an LED indicator, and hardware-based real-time data compression and encoding apparatus so that compressed video data may be transmitted in an appropriate format such as an intra-image based MPEG (motion picture expert group) standard for decoding by the system unit 1400. The camera LED indicator is arranged to illuminate in response to appropriate control data from the system unit 1400, for example to signify adverse lighting conditions. Embodiments of the video camera 1412 may variously connect to the system unit 1400 via a USB, Bluetooth or Wi-Fi communication port. Embodiments of the video camera may include one or more associated microphones and also be capable of transmitting audio data. In embodiments of the video camera, the CCD may have a resolution suitable for high-definition video capture. In use, images captured by the video camera may for example be incorporated within a game or interpreted as game control inputs. In another embodiment the camera is an infrared camera suitable for detecting infrared light.

In general, in order for successful data communication to occur with a peripheral device such as a video camera or remote control via one of the communication ports of the system unit 1400, an appropriate piece of software such as a device driver should be provided. Device driver technology is well-known and will not be described in detail here, except to say that the skilled man will be aware that a device driver or similar software interface may be required in the present embodiment described.

Embodiments of the present invention may be practiced with various computer system configurations including hand-held devices, microprocessor systems, microprocessor-based or programmable consumer electronics, minicomputers, mainframe computers and the like. The invention can also be practiced in distributed computing environments where tasks are performed by remote processing devices that are linked through a network.

With the above embodiments in mind, it should be understood that the invention can employ various computer-implemented operations involving data stored in computer systems. These operations are those requiring physical manipulation of physical quantities. Any of the operations described herein that form part of the invention are useful machine operations. The invention also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data maybe processed by other computers on the network, e.g., a cloud of computing resources.

One or more embodiments of the present invention can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing invention has been described in some detail for purposes of clarity of understanding, it will be apparent that certain changes and modifications can be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A method for configuring a computer program based on a user, the method comprising:
    entering a signature detection mode by the computer program;
    detecting a signature entered by the user, the signature entered by moving a controller held by the user;
    exiting the signature detection mode;
    determining if the computer program has user information associated with the signature entered by the user; and
    setting a new calibration for the controller in the computer program based on the user information when the computer program has the user information for the signature entered by the user.

2. The method as recited in claim 1, wherein setting a calibration for the controller includes:
    setting the new calibration for the controller without the user performing new calibrating operations.

3. The method as recited in claim 2, wherein setting the calibration for the controller includes:
    setting a value for a size of the user in the computer program.

4. The method as recited in claim 1, wherein the computer program is embedded in a non-transitory computer-readable storage medium.

* * * * *